(12) United States Patent
Sabado et al.

(10) Patent No.: US 10,716,624 B2
(45) Date of Patent: Jul. 21, 2020

(54) MINIMALLY INVASIVE CONTRACEPTION METHOD AND DEVICE

(75) Inventors: Martin Sabado, Haverhill (GB); Wolfgang Neuberger, Dubai (AE)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 923 days.

(21) Appl. No.: 13/101,873

(22) Filed: May 5, 2011

(65) Prior Publication Data

US 2012/0283619 A1 Nov. 8, 2012

(51) Int. Cl.
| | | |
|---|---|---|
| *A61M 37/00* | (2006.01) | |
| *A61B 18/20* | (2006.01) | |
| *A61B 18/22* | (2006.01) | |
| *A61B 18/24* | (2006.01) | |
| *A61B 18/00* | (2006.01) | |
| *A61B 90/00* | (2016.01) | |

(52) U.S. Cl.
CPC ............. *A61B 18/22* (2013.01); *A61B 18/24* (2013.01); *A61B 2018/00559* (2013.01); *A61B 2018/00642* (2013.01); *A61B 2018/00702* (2013.01); *A61B 2018/00791* (2013.01); *A61B 2018/00982* (2013.01); *A61B 2090/378* (2016.02); *A61B 2218/001* (2013.01)

(58) Field of Classification Search
CPC ............. A61B 18/22; A61B 2018/001; A61B 2018/00559; A61B 2018/00642; A61B 2018/00702; A61B 2018/00791; A61B 2018/00982; A61B 2018/2255; A61B 2019/5276; A61B 2218/001; A61B 2090/378

USPC .......................... 606/2, 3, 8, 10–18; 128/898
See application file for complete search history.

(56) References Cited

U.S. PATENT DOCUMENTS

| | | | |
|---|---|---|---|
| 4,269,174 A | * | 5/1981 | Adair ................... A61B 18/082 128/842 |
| 5,147,353 A | * | 9/1992 | Everett .................. A61B 18/24 128/831 |
| 5,556,396 A | | 9/1996 | Cohen et al. |
| 5,601,600 A | | 2/1997 | Ton |
| 5,746,769 A | | 5/1998 | Ton et al. |

(Continued)

*Primary Examiner* — Erica S Lee
(74) *Attorney, Agent, or Firm* — BJ Associates; Bolesh J. Skutnik

(57) ABSTRACT

Minimally invasive methods and devices for endoluminally treating female fallopian tubes or male vas deferens of mammals are presented as a permanent method of contraception. In preferred embodiments, medical devices for male and female sterilization comprise laser radiation source operating at one or more preselected wavelengths between about 980 nm and about 1950 nm, preferably at least one of 980 nm, 1470 nm and 1950 nm; treatment waveguide with a radial or cylindrical radiation emitting tip; viewing scope; and a temperature sensor. In another preferred embodiment, a minimally-invasive permanent contraception method for males and females comprises the steps of introducing at least one treatment waveguide in a body cavity; positioning the treatment waveguide inside a body cavity; irradiating; and repeating the procedure in companion body cavity to inhibit fertilization. In another embodiment, fluids are infused and/or extracted after, before or during the procedure to enhance laser energy absorption and enhance efficiency of laser treatment.

6 Claims, 3 Drawing Sheets

(56) References Cited

U.S. PATENT DOCUMENTS

| | | | |
|---|---|---|---|
| 5,897,551 A * | 4/1999 | Everett et al. | 606/15 |
| 6,042,590 A * | 3/2000 | Sporri | A61B 17/12022 |
| | | | 606/135 |
| 6,096,052 A | 8/2000 | Callister et al. | |
| 6,112,747 A * | 9/2000 | Jones et al. | 128/898 |
| 6,176,240 B1 | 1/2001 | Nikolchev et al. | |
| 6,352,549 B1 | 3/2002 | Everett | |
| 6,378,524 B1 * | 4/2002 | Jones | A61B 18/24 |
| | | | 128/830 |
| 6,432,116 B1 | 8/2002 | Callister et al. | |
| 6,526,979 B1 | 3/2003 | Nikolchev et al. | |
| 6,634,361 B1 | 10/2003 | Nikolchev et al. | |
| 6,679,266 B2 | 1/2004 | Nikolchev et al. | |
| 6,684,884 B2 | 2/2004 | Nikolchev et al. | |
| 6,705,323 B1 | 3/2004 | Nikolchev et al. | |
| 6,871,650 B1 | 3/2005 | Nikolchev et al. | |
| 8,202,268 B1 * | 6/2012 | Wells | A61B 18/22 |
| | | | 606/10 |
| 8,257,347 B2 * | 9/2012 | Neuberger | A61B 18/22 |
| | | | 606/15 |
| 2009/0240242 A1 * | 9/2009 | Neuberger | A61B 18/24 |
| | | | 606/7 |
| 2011/0152979 A1 * | 6/2011 | Driscoll | A61N 5/0616 |
| | | | 607/93 |
| 2014/0012077 A1 * | 1/2014 | Fagnani | A61B 18/22 |
| | | | 600/108 |

\* cited by examiner

MINIMALLY INVASIVE CONTRACEPTION METHOD AND DEVICE

BACKGROUND OF THE INVENTION

1. Field of the Invention

The present invention relates to devices and methods for sterilization as a permanent method of contraception. More particularly, present invention provides minimally invasive methods and medical devices for endoluminally treating female fallopian tubes or male vas deferens of a mammal as a permanent method of contraception involving radiation energy delivery.

2. Invention Disclosure Statement

Nowadays, numerous women in childbearing age are able to decide when they would like to become pregnant by choosing an appropriate contraception method according to its efficacy, safety, personal preference, cost and non-contraceptive benefits. Birth control methods are generally based on either preventing a male's sperm, from reaching and entering a female's egg or preventing the fertilized egg from implanting in the female's uterus and starting to grow. Some of these contraception methods are reversible such as oral contraceptives, diaphragms, intrauterine devices (IUD), hormonal intrauterine systems (IUS), condoms and hormonal implants whereas others are characterized 'permanent' because they result in permanent or irreversible condition.

Sterilization is considered a permanent method of contraception and is generally intended for women who are satisfied with their number of children, feel too mature to have any, or have a life-threatening medical condition and cannot risk becoming pregnant. Among the different types of permanent contraception methods available, surgical sterilization in the form of tubal ligation for women and vasectomy for men serve to prevent sperm from joining the unfertilized egg. The fallopian tubes for women and vas deferens for men may be tied, cut, clamped, cauterized or blocked. There are different techniques for tubal ligation like the Pomeroy technique and its modified versions which involves tying a segment of tube with an absorbable ligature and then removing it. In general, tubal ligation involves more risks for women than vasectomy for men as the procedure requires an abdominal incision usually performed under general anesthesia in a hospital setting, most often at a day surgery unit. Potential complications from tubal ligation involve all the risks associated with surgery, including bleeding, infection and general anesthesia inconveniences. Alternatively, instead of removing a segment of the tube other mechanical methods such as tubal rings or clips may be applied to the fallopian tubes through a laparoscope. Other laparoscopic methods of tubal ligation includes bipolar or monopolar coagulation in which the fallopian tube is grasped between two poles of electrical conducting forceps and electrical current passes through the tube between the two ends of the forceps, damaging that segment of tube. Even though laparoscopic methods provide many advantages compared to traditional tubal ligation surgery, these procedures still require one or more incisions to insert the laparoscope and perform the sterilization. Unfortunately, mini-laparotomy patients may also suffer from complications such as infection, injury to the bladder or bleeding from a major blood vessel, and burning of the bowel or other structures as well as anesthesia complications.

In an attempt to provide medical devices and methods for performing sterilization of a patient, U.S. Pat. No. 6,352,549 by Everett discloses a localized heat applying medical device for applying heat to tissue adjacent a patient's tubal ostia in order to close the patient's fallopian tubes. The device includes a bulbous heating generating device connected to a Nd:YAG laser source which closes the fallopian tube mainly by heat. One disadvantage is the need of a bulbous heat generating device that may be uncomfortable or dangerous while placing it in appropriate position, as tissue walls may be damaged or perforated while positioning it in the desired location. Furthermore, whereas on one hand the device relies on fixed contact with the tissue adjacent the tubal ostia to transmit heat and coagulate the tissue, on the other hand the device also transmits an additional portion of the light energy through a frontal aperture that can lead to a lack of control of the extension of the damaged area and can destroy the tissue creating holes. Additionally, in order to be effective the heat generating device needs to be maintained in fixed contact with the tissue for a substantial time while heat is transmitted to tissue, disadvantageously adding more time to the whole procedure. Accordingly, it would be desirable to provide a device with soft edges and appropriate size that can effectively and accurately deliver light energy to treatment areas in a reasonable period of time, while at the same time provide precise control of the extent and site of damage.

A method for electro-ligation of a fallopian tube is disclosed in U.S. Pat. No. 5,556,396 by Cohen et al. Briefly described, the method includes the steps of providing an electrically energizable electrode and an instrument, and disposing the electrode in the instrument. Then, advancing the electrode and the instrument into the fallopian tube such that the electrode is juxtaposed with the wall of the fallopian tube and energizing the electrode until the fallopian tube collapses around the electrode to block the fallopian tube without perforating it. In this case, an electrode is used which is energized by a power supply. As with most electrical type devices and procedures, good contact must be established and kept with the walls in order to get proper operation. This can be a problem in many cases. Where functioning is as a 'hot poker', there is the danger of excess contact and potential piercing walls before closure.

There are other contraceptive or sterilization devices which occlude the reproductive lumen such as the devices disclosed in U.S. Pat. Nos. 6,432,116 B1 and 6,096,052 by Callister et al. In these examples, the device consists of a mesh member and a tubular member that allows the in-growth of tissue which produces a tissue impregnated mesh occluding the body lumen, thus the tissue impregnating the mesh forms the occluding member. Other examples include copper or copper alloy intrafallopian devices disclosed in U.S. Pat. Nos. 6,871,650, 6,679,266, and 6,176,240 by Nikolchev et al; copper or copper alloy intra-fallopian devices which can effect permanent sterilization by passing a current through a resilient structure to the tubal wall disclosed in U.S. Pat. Nos. 6,705,323, 6,684,884, 6,634,361 and 6,526,979, U.S. by Nikolchev et al; and endoluminal coil delivery systems disclosed in U.S. Pat. No. 5,746,769 by Ton et al and U.S. Pat. No. 5,601,600 by Ton. Unfortunately, effectiveness relies on how well the tissue impregnates the mesh or requires the device is properly placed, leading to only a moderately effective method for preventing pregnancies. Furthermore, since tissue growth requires time, an additional contraception method must be used for about 3 months after procedure. Additionally, such devices may cause bleeding, pain or damage as they may penetrate the delicate tissue inside fallopian tubes.

The present invention overcomes prior art drawbacks; providing effective, safe and minimally invasive permanent contraceptive methods and devices to be performed as an outpatient procedure without general anesthesia, producing scarce or null scars and avoiding the need of concomitant long-term hormone administration.

OBJECTIVES AND BRIEF SUMMARY OF THE INVENTION

It is an objective of the present invention to provide effective, safe and minimally invasive methods and devices for permanent contraceptive treatment of female and male mammals.

Yet, another objective is to endoluminally treat female's fallopian tubes or male's vas deferens of mammals with laser energy, in order to provide a more effective, safer and minimally invasive sterilization method compared to prior art procedures.

Still another objective is to provide minimally invasive sterilization methods for sterilization to be performed as an outpatient procedure without needing general anesthesia, producing scarce or null scars and avoiding the necessity of concomitant long-term hormone administration.

A further objective is to provide medical devices to deliver laser radiation energy in a direct and efficient manner into the fallopian tube and vas deferens wall tissues, substantially avoiding any significant amount of radiation absorption by the surrounding tissues.

Briefly stated, the present invention provides minimally invasive methods and devices for endoluminally treating female fallopian tubes or male vas deferens of mammals as a permanent method of contraception. In preferred embodiments, medical devices for male and female sterilization comprise laser radiation source operating at one or more preselected wavelengths between about 980 and about 1950 nm, preferably at least one of 980, 1470 and 1950 nm; a treatment waveguide with radial or cylindrical radiation emitting tip; viewing scope; and a temperature sensor. In another preferred embodiment, a minimally-invasive permanent contraception method for males and females comprises the steps of introducing at least one treatment waveguide in a body cavity; positioning the treatment waveguide inside a body cavity; irradiating; and repeating the procedure in companion body cavities to inhibit fertilization. In another embodiment, fluids are infused or extracted after, before or during the procedure to enhance laser energy absorption and enhance efficiency of laser treatment.

The above, and other objects, features and advantages of the present invention will become apparent from the following description read in conjunction with the accompanying drawings, (in which like reference numbers in different drawings designate the same elements.)

DETAILED DESCRIPTION OF PREFERRED EMBODIMENTS

As described further below, the present invention provides minimally invasive methods and medical devices for safe and efficient endoluminal treatment of the fallopian tubes in female mammals and vas deferens in male mammals for permanent contraception. A key feature of present invention is the possibility of endoluminally treating the fallopian tubes or vas deferens for sterilization as an outpatient procedure without needing general anesthesia, producing scarce or null scars and avoiding the necessity of concomitant long-term hormone administration or additional contraceptive methods. Moreover, the present invention methods and devices provide safer and more efficient sterilization procedures than traditional fallopian tube ligation surgery or laparoscopic approaches, significantly diminishing the risks associated with prior art alternatives. With this invention, the fallopian tube or the vas deferens lumen are endoluminally damaged, reducing its diameter sufficiently to inhibit fertilization or closing the lumen immediately after the procedure. After the treatment, the damaged tubes or lumens gradually change into fibrotic, tissue producing the desired permanent diameter reduction and/or closure of the tubes or lumens.

Figure 1:
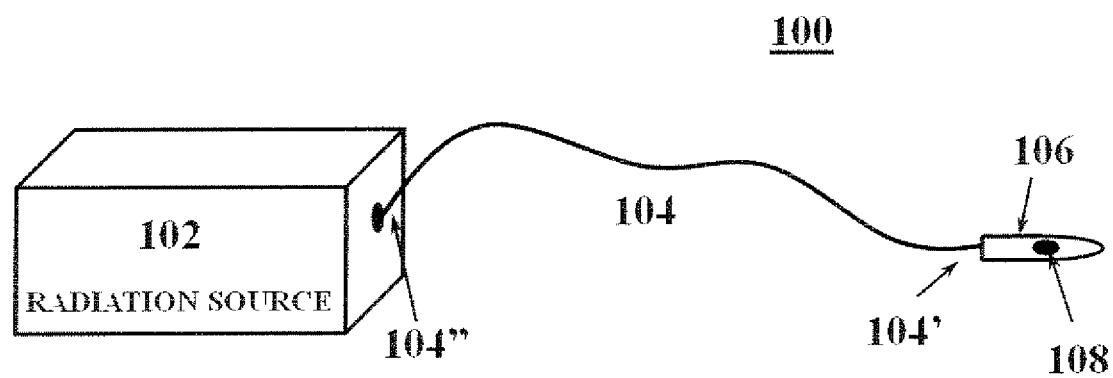
FIG. 1—shows one embodiment of present invention, comprising a medical device for minimally-invasive permanent contraception treatments.

In a preferred embodiment, a medical device 100 for male or female mammal sterilization by endoluminally treating the vas deferens or fallopian tubes as shown in FIG. 1 comprises radiation source 102; at least one treatment waveguide 104 with distal end 104' and proximal end 104" and radial or cylindrical radiation emitting tip 106 at treatment waveguide 104 distal end 104', comprising a variable radiation emission section and temperature sensor 108. In case of female sterilization, the device further includes a viewing or imaging scope, such as a hysteroscope or falloscope, for guiding the treatment waveguide 104 to the treatment site i.e. desired position inside fallopian tubes.

Radiation source includes coherent radiation sources, preferably laser radiation sources whose output is or can be regulated within a selected spectral window. In a preferred embodiment, radiation source is a diode laser radiation source of wavelength between about 980 and about 1950 nm operating in continuous or pulse mode. In another embodiment, the diode laser radiation source operates at a wavelength preselected from the group consisting of about 980±30 nm, about 1470±50 nm, and about 1950±50 nm. In another embodiment, diode laser radiation source operates at two or more different wavelengths selected form the range between about 980 and 1950 nm, e.g. 980±30 nm and 1470±50 nm, in order to simultaneously or continuously irradiate different target tissues to enhance the desired contraceptive effect.

In another embodiment, diode laser radiation source operating at between about 1470±50 nm and 1950±50 nm is preferred because within these wavelengths laser radiation energy is highly absorbed by water, and within vessel walls, providing laser wavelength absorption with sufficient energy to heat water inside the fallopian tube and vas deferens wall tissues and denature proteins, such as collagen, in the target wall tissues. As a result, laser radiation is directly transmitted into and absorbed by the surrounding annular portion of the fallopian tube or vas deferens wall tissues or otherwise by a sufficient depth of endothelium to damage the absorbing endothelium and, in turn, achieve fallopian tube or vas deferens lumen diameter reduction and/or closure to inhibit fertilization. The terms fallopian tube or vas deferens lumen closure, close the fallopian tube or vas deferens lumen, occlude the fallopian tube or vas deferens lumen, or like terms, are used herein to mean closure and/or shrinkage of the fallopian tube or vas deferens lumen that is sufficient to substantially prevent the passage of eggs through the fallopian tube in females or the flow of sperm through vas deferens lumen following treatment of the fallopian tube or vas deferens, respectively, and thus inhibit the possibility of fertilization. A further advantage is that, at the laser wavelengths employed, the laser energy delivery allows the release of sufficiently high energy to close or reduce the diameter of the vas deferens lumen or fallopian tube of mammals, but it is sufficiently low to avoid the need of general or periluminal anesthetics along the treated length of lumen or tube. Nonetheless, as pain sensation is of subjective nature and consequently substantially patient-dependent, local anesthetic or sedation could be included for highly sensitive patients.

Treatment waveguides are preferably optical fibers which deliver laser radiation at treatment site. Treatment waveguides are preferably manufactured and used in accordance with the invention disclosed in commonly assigned US patent publication N° 2009/0240242-A1, published 24 Sep. 2009, titled "Endoluminal Laser Ablation Device and Method for Treating Veins", which is hereby incorporated by reference in its entirety as part of the present disclosure. Yet another advantage is that because the laser radiation is directly and efficiently transmitted into and absorbed by the fallopian tube and vas deferens wall tissues, any significant amount of radiation absorption by the surrounding tissues, and resulting thermal damage, is substantially avoided. Moreover, as the extent of laser energy emission is precisely defined by the size of the emitting radial or cylindrical surface of the optical fiber tip, more control of the extension and location of the treated section is obtained.

In a preferred embodiment, a minimally-invasive method for male and female sterilization of a mammal comprises the steps of:
 a) introducing at least one treatment waveguide in a body cavity;
 b) positioning said at least one treatment waveguide in a preselected treatment site inside said body cavity;
 c) irradiating said body cavity;
 d) repeating the procedure in companion body cavity to inhibit fertilization.

The proximal end of said waveguide is connected to a radiation source and the distal end of said waveguide has a variable radiation emission section. Preferably, treatment waveguide is an optical fiber with proximal and distal ends and the radiation source is a diode laser radiation source. Preferably, the laser radiation source operates in continuous or pulse mode with one or more preselected wavelengths between about 980 nm and about 1950 nm; and treatment waveguides are preferably optical fibers manufactured and used in accordance with the invention disclosed in commonly assigned US patent publication N° 2009/0240242-A1 as stated above. Irradiation parameters are set according to the diameter of said body cavity. The preferred body cavities to be treated with the present method are the fallopian tubes and the vas deferens. While irradiating in step c), the optical fiber may be progressively pulled back in order to provide a continuous linear endoluminal laser energy density over an extended length of tubes or vas deferens.

Figures 2, 2A:
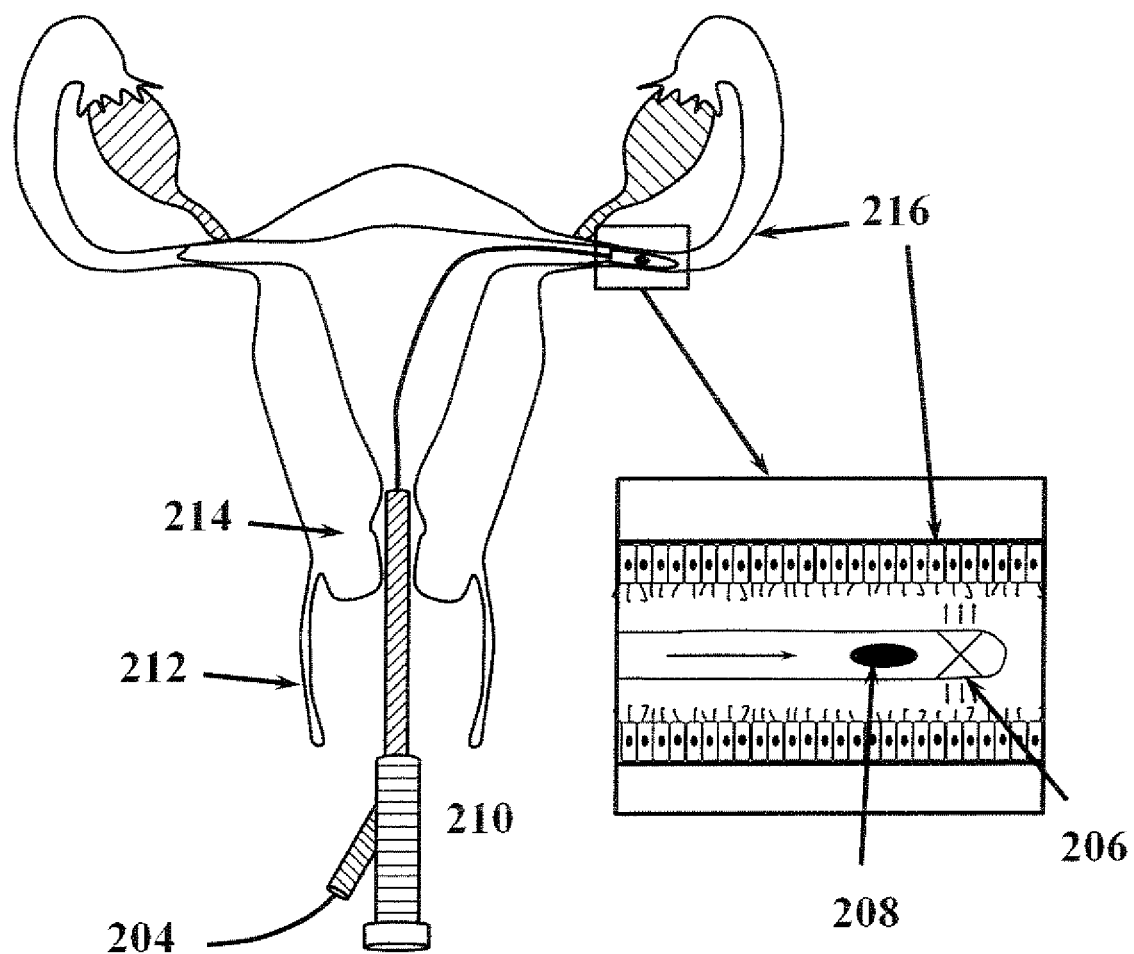
FIG. 2—shows one embodiment of present invention, comprising a minimally-invasive permanent contraception method for females.
FIG. 2a shows a view of the embodiment shown in FIG. 2.

In another embodiment, a method for female sterilization of a mammal further comprises the step of guiding the treatment waveguide with the aid of a viewing scope, such as a falloscope or a hysterocope. The viewing scope is used in order to transcervically position the treatment waveguide in the desired position inside the fallopian tube carefully passing through the vagina and cervix up to fallopian tube using appropriate dilation procedure. Advantageously, accessing the fallopian tube through the vagina and cervix completely avoids the need to make incisions which would rupture the skin, highly reducing potential infections or scarring. FIG. 2 shows how treatment waveguide 204 is advanced with the aid of imaging scope 210 through transvaginal path 212 and trans-cervical path 214 up inside fallopian tube 216. Thus, there is no need of cutting or making incisions in order to introduce the treatment waveguide as in laparoscopic procedures or surgeries, and the costs, potential for infections and pain, need for anesthesia and other undesired factors associated with invasive procedures are avoided. In addition, FIG. 2a on the right shows treatment waveguide 204, its radial or cylindrical radiation emitting tip 206 and temperature sensor 208 inside fallopian tube 216. Temperature sensor 208 is preferably close to radial or cylindrical radiation emitting tip 206 as the information registered by the sensor inside the fallopian tube is processed, for example by a radiation source control unit, and then is used to control the radiation energy delivered to the treatment site.

Additionally, water absorption inside fallopian tube or vas deferens lumen can be enhanced by the infusion of an infusing fluid that can absorb the emitted laser energy and/or may enhance laser energy absorption by the target tissue. Infusion fluid is generally an aqueous solution, isotonic, hypertonic or hypotonic solution more preferably a saline solution, or may be any substance/solution that can absorb the emitted radiation, i.e. a preselected chromophore solution. Thus in one embodiment, the viewing scope used to view and conduct the treatment waveguide has additional conduits for infusing fluids or extracting fluids after, before or during the procedure. Thus, the infusion fluid is used for distending the uterus and allow video monitoring and to enhance laser energy absorption by the body cavity walls.

In another embodiment, male and female sterilization methods include and use additional means for placing treatment waveguide such as guide wires, introducer sheaths or catheters, as well as locking systems allowing correct relative positioning between treatment waveguide and said additional placing means. However, due to the nature of the distal portion of the tip of present invention, insertion through vas deferens lumen or fallopian tube is facilitated, thus the need of additional placing means may be eliminated in many, if not all instances, from the procedure.

Figure 3:
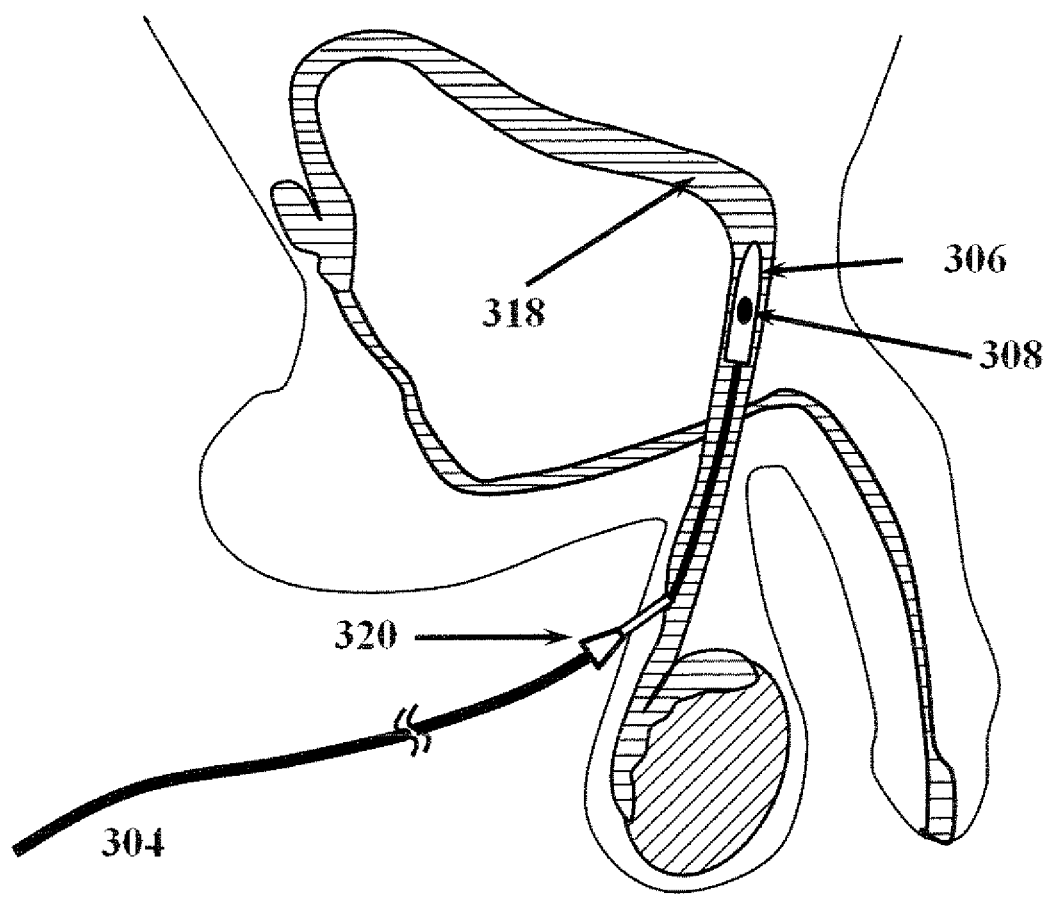
FIG. 3—shows one embodiment of present invention, comprising a minimally-invasive permanent contraception method for males.

In another embodiment shown in FIG. 3, a method for male sterilization further comprises the step of accessing vas deferens lumen 318 with the aid of introducer needle 320 or similar. Then, treatment waveguide 304 is advanced through vas deferens lumen 318 positioning its radial or cylindrical radiation emitting tip 306 in the desired treatment site. Temperature sensor 308 allows monitoring the temperature inside vas deferens lumen for radiation control purposes. The procedure may be done entirely under ultrasound guidance in order to monitor progress inside vas deferens lumen of introducer needle and treatment waveguide and check appropriate positioning of these elements inside vas deferens lumen. A significant advantage is that neither tumescent anesthesia nor general anesthesia is required, only a small amount of local anesthesia may be applied at the access site. The present invention is further illustrated by the following examples, but is not limited thereby.

Example 1

In one example, the vas deferens to be treated is identified and marked under ultrasound guidance. Then, a conical dilator is inserted into a catheter until the end part of the dilator protrudes from the catheter a predetermined distance. Then, an access site is created with the aid of a needle and local intradermal anesthesia is administered at this site. After vas deferens puncture, a guide wire is introduced into vas deferens lumen, monitoring progress with ultrasound guidance. Next, the needle is removed and a dilator-catheter assembly is fit onto the guide wire and is advanced to a preselected treatment site inside vas deferens lumen. After that, the conical dilator and the guide wire are withdrawn while the catheter is left in place, checking the correct position with ultrasound guidance. Subsequently, the proximal end of a radial optical fiber is connected to a diode laser of 1470 nm and the distal end of the radial optical fiber is introduced into the catheter. Radial optical fiber's tip is advanced until matching the catheter's tip and then the catheter is withdrawn a predetermined distance, leaving the distal tip of the radial optical fiber exposed. According to diameter of the vas deferens lumen and its depth below the skin, the laser parameters are set. Next, laser radiation is applied while withdrawing the fiber-catheter assembly with the appropriate pull back speed. Then, the skin at the site of entry is closed with the aid of a sterile strip dressing. Finally, the left vas deferens was treated with the same procedure.

Example 2

In the case of canines or felines, oral medications manufactured specifically for birth control can have serious unwanted side effects, are expensive, and usually cannot be used for long periods of time. Thus, surgical sterilization is frequently employed. Taking as an example the case of female canines or felines, surgical sterilization procedures commonly chosen include ovariohysterectomy, in which both the ovario and the uterus are removed, and hysterectomy, in which only the uterus is removed; or tubal ligation. Even though laparoscopic tubal ligation is less invasive than ordinary surgical sterilization procedures, it is not common among veterinarians as there is not widespread experience in the subject. Main disadvantages of these invasive surgical procedures include the need of general anesthesia, generally using a breathing tube in the trachea that is connected to an anesthesia machine; a large incision in the abdominal area; overnight stay in the veterinary; and long healing recovery time typically between about 10 to 14 days. Other complications can include fever, pain, skin irritation to the sutures, or reaction to the anesthesia (typically throwing up), and in extreme cases death from unpredictable anesthetic reaction, excessive bleeding, or an abdominal infection. In order to overcome these disadvantages the method described below is an example of a safe and minimally-invasive permanent sterilization procedure which can be performed in a female canine. Firstly, a section of the fallopian tube to be treated is identified and selected. Then, a set consisting of a cannula, a falloscope and a radial optical fiber is guided through the vagina and cervix up to a predetermined section of the fallopian tube using appropriate dilation methods. With the aid of the falloscope the fiber's tip located at the distal end of the radial optical fiber is advanced until matching the cannula's tip and then the cannula is withdrawn a predetermined distance, leaving the distal tip of the radial optical fiber exposed. Then the falloscope is removed and the radial optical fiber and cannula are left in place. The proximal end of the radial optical fiber is connected to a diode laser operating at about 1470 nm. According to diameter of the fallopian tube and its depth below the skin, the laser parameters are set. Next, laser radiation is applied while withdrawing the fiber-cannula assembly with the appropriate pull back speed. Then, the companion fallopian tube is treated following the same procedure.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A minimally-invasive permanent contraception method for male/female mammals comprising the steps of;
    a) endoluminally introducing at least one treatment waveguide connected to a laser radiation source and having a radial or cylindrical laser radiation emitting tip, in a fallopian tube or vas deferens lumen;
    b) positioning said at least one treatment waveguide in a preselected treatment site inside said fallopian tube or vas deferens lumen;
    c) infusing into said fallopian tube or vas deferens lumen an infusion liquid selected as any substance/solution that can absorb the emitted radiation selected from the group of aqueous solutions, isotonic solutions, hypertonic solutions, hypotonic solutions, preselected chromophore solutions and combinations of these;
    d) while progressively pulling back the treatment waveguide, endoluminally irradiating said fallopian tube or vas deferens lumen with laser radiation of at least two different wavelengths selected from the group consisting of 980+/−30 nm. 1470+/−50 nm and 1950+/−50 nm, the laser radiation having sufficient energy to denature proteins in said fallopian tube or vas deferens lumen, whereby a continuous linear endoluminal laser energy density is provided over an extended length of the fallopian tube or vas deferens;
    e) using measurements from a temperature sensor to control irradiation of said fallopian tube or vas deferens lumen; said temperature sensor being disposed in proximity to the radial or cylindrical laser radiation emitting tip irradiating said fallopian tube or vas deferens lumen; and
    f) repeating the procedure to achieve reduction or closure of the fallopian tube or vas deferens and thus inhibit fertilization.

2. The minimally-invasive permanent contraception method for male/female mammals according to claim 1, wherein said step of positioning of treatment waveguide is performed under suitable imaging means selected from the group consisting of ultrasound, viewing scopes and combinations of them.

3. The minimally-invasive permanent contraception method for male/female mammals according to claim 1, wherein said step of positioning of treatment waveguide comprises positioning of treatment waveguide using additional means selected from the group consisting of guide wires, introducer sheaths, catheters and combinations of them.

4. The medical minimally-invasive permanent contraception method for male/female mammals according to claim 1, wherein said treatment waveguide is at least one optical fiber with a distal and a proximal end, and with a variable radiation emission section in the vicinity of its distal end.

5. The medical minimally-invasive permanent contraception method for male/female mammals according to claim 1, wherein said radiation has wavelengths consisting of 980±30 nm and 1950±50 nm.

6. The medical minimally-invasive permanent contraception method for male/female mammals according to claim 1, wherein the wavelengths of said radiation consist of 1470±50 nm and 1950±50 nm.

\* \* \* \* \*